United States Patent
Baber

[11] Patent Number: 5,246,015
[45] Date of Patent: Sep. 21, 1993

[54] MALE IMPOTENCY AID

[76] Inventor: Paul H. Baber, 353 Oakcrest La., Roseville, Minn. 55113

[21] Appl. No.: 917,495

[22] Filed: Jul. 21, 1992

[51] Int. Cl.⁵ .......................... A61F 6/02; A61F 5/00
[52] U.S. Cl. ...................................... 128/842; 600/39
[58] Field of Search .................. 128/842, 844, 918; 604/347–353; 600/38, 39

[56] References Cited

U.S. PATENT DOCUMENTS

| | | | |
|---|---|---|---|
| 602,917 | 4/1898 | Scheinkman | 600/39 |
| 1,585,861 | 5/1926 | Huff | 600/39 |
| 2,471,360 | 5/1949 | Thorne | 600/39 |
| 2,586,674 | 2/1952 | Lönne | 128/844 |
| 2,899,957 | 8/1959 | Briggs | 600/39 |
| 3,131,691 | 5/1964 | Scott | 600/39 |
| 3,401,687 | 9/1968 | Hood | 600/39 |
| 3,636,948 | 1/1972 | Atchley | |
| 3,683,901 | 8/1972 | Wegener | 600/39 |
| 3,759,253 | 9/1973 | Cray | |
| 3,939,827 | 2/1976 | Brunstetter | |
| 4,203,432 | 5/1980 | Koch | |
| 4,224,933 | 9/1980 | Reiling | 600/39 |
| 4,539,980 | 9/1985 | Chaney | |
| 4,723,538 | 2/1988 | Stewart et al. | |
| 4,821,742 | 4/1989 | Phelps | 128/842 |
| 4,834,115 | 5/1989 | Stewart | |
| 4,893,616 | 1/1990 | Immonen | |
| 4,960,113 | 10/1990 | Seeberg-Elverfeldt | |
| 4,967,738 | 11/1990 | March | |
| 4,995,381 | 2/1991 | Marmar et al. | |
| 5,027,800 | 7/1991 | Rowland | |
| 5,074,315 | 12/1991 | McCuiston | 128/844 |

Primary Examiner—Michael A. Brown
Attorney, Agent, or Firm—Merchant, Gould, Smith, Edell, Welter & Schmidt

[57] ABSTRACT

A male impotency aid device for enabling a man to acquire and maintain an erect penis which has a rigid tubular portion having an inner surface that is sized to fit snugly on the penis without strangulation and that has an inner surface with a notch extending the length of the tubular member that is aligned with the penile urinary tract and which has an annular rim that extends outward from the outer surface of the tubular portion. The device is applied over the penis such that an end surface on the tubular portion comes into contact with the crus of the user's penis to stimulate the penis to obtain an erection without strangulation. The inner surface then acts to limit the bloodflow from the penis to help maintain the erection, also without strangulation.

3 Claims, 2 Drawing Sheets

MALE IMPOTENCY AID

FIELD OF INVENTION

This invention relates to therapeutic devices for assisting males to obtain and maintain an erect penis.

BACKGROUND OF INVENTION

The achievement and maintenance of an erection in the male penis is generally related to the inflow and the outflow of blood in the penis. Upon stimulation, the nerve endings in the penis release a neurotransmitter that causes the main artery in the corpus cavernosum to dilate, which increases the bloodflow to the penis. As the bloodflow increases, the penis starts to become erect and the veins that normally drain the blood from the penis are pressed against the capsule of the erectile bodies preventing the draining of blood from the penis, thereby maintaining the erection.

The most typical cause of sexual impotency in males is leakage from the veins in the penis. This leakage enables blood to flow from the penis, preventing the attainment of an erection or causing a premature loss of an erection. This leakage can either be remedied surgically or by the use of devices that are applied over the penis.

Many of these impotency aid devices are designed to cut off the vein leakage through strangulation of the penis. Unfortunately, these devices can also cut off the bloodflow to the artery feeding the penis, and if so, they can damage the penis. Moreover, the corpus spongiosum, which is located on the underside of the penis and which contains the penile urinary tract from which ejaculate flows, does not become rigid during an erection. Therefore, these strangulation type devices can also prevent or inhibit ejaculation. In addition, these devices are usually only available in one size, therefore, the effectiveness of the device and the detriments associated with the device vary with the size of the penis.

Many of the other devices that are currently used are either costly, complicated to apply or are cumbersome so that they can interfere with the mutual enjoyment experienced by both partners. Therefore, there arises a need for an effective male impotency aid that does not act by strangulating the penis, that is easily applied, that is not so cumbersome as to interfere with the sex act for either party and that is low cost with multiple fitting sizes.

BRIEF SUMMARY OF INVENTION

The present invention is for a male impotency aid device having a rigid tubular portion that is sized to fit snugly over the penis without strangulation and that has a notch located on the inner surface of the tubular portion that is aligned with the penile urinary tract. The device also has an annular rim which extends outward from the outer surface of the tubular portion to make the device easy to apply. This simple design results in low cost yet effective device. The small size of the device also renders it all but undetectable by either party during the sex act.

The present invention is easily applied by sliding it over the penis until the end surface of the tubular portion is in contact with the crus of the penis. The contact of the end surface on the crus of the penis stimulates the penis to help achieve an erection. The snug fit also helps to limit the leakage flow in the veins to further aid in achieving and maintaining an erection. However, because the device is specially sized so as not to be strangulating, the danger of cutting off bloodflow to the arteries is eliminated. In addition, because the notch is aligned with the penile urinary tract, pressure is not placed on the urinary tract and normal ejaculation is not inhibited.

The present invention is further explained hereinafter with more particularity and by reference to the preferred embodiment shown in the following drawings.

DETAILED DESCRIPTION OF THE PREFERRED EMBODIMENT

Figure 1:
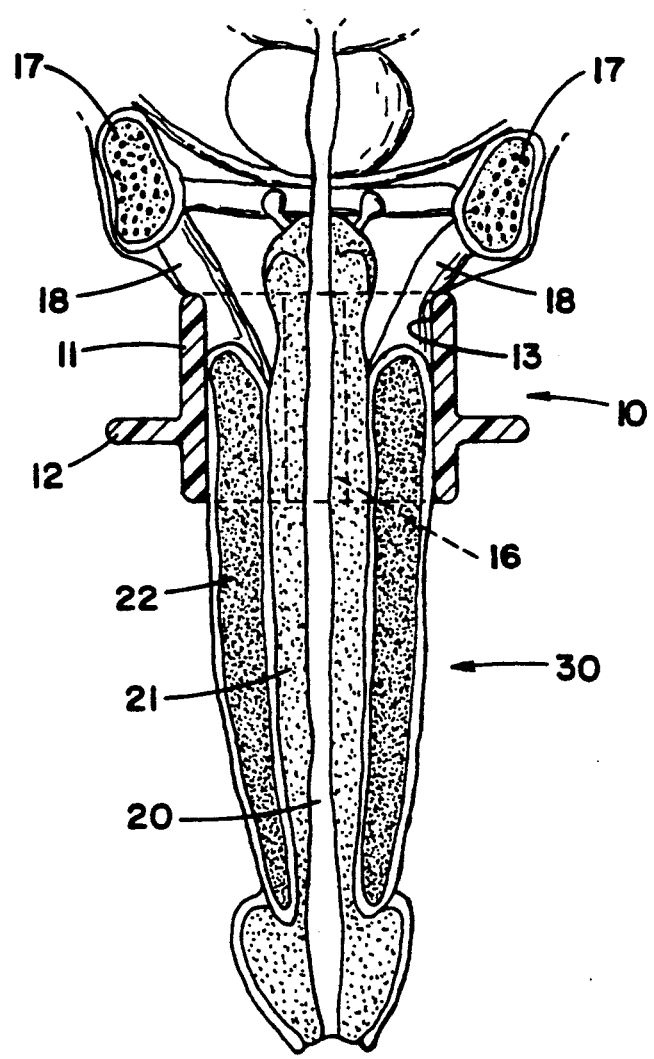
FIG. 1 is a cross-sectional view of the preferred embodiment of the invention as shown on the penis in its applied position with portions cut away.
Figure 2:
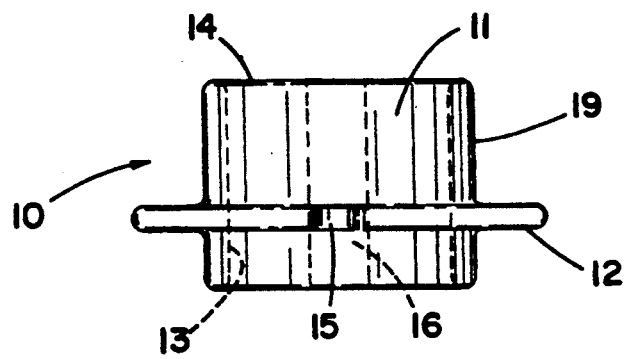
FIG. 2 is a view in side elevation of the preferred embodiment of the invention.
Figure 3:
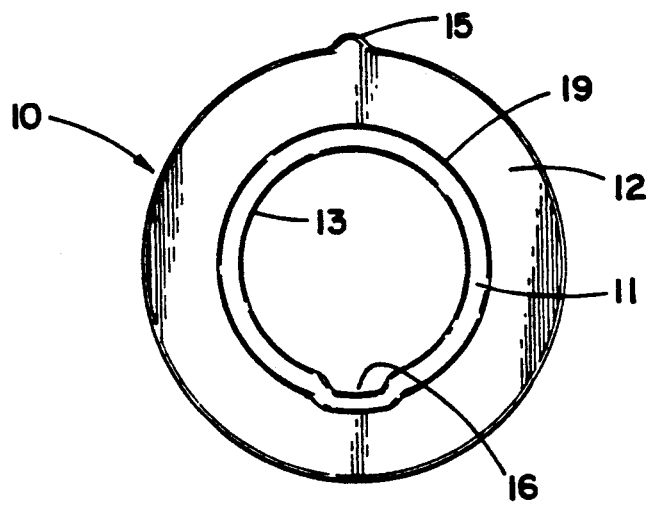
FIG. 3 is a end view of preferred embodiment of the invention.
Figure 4:
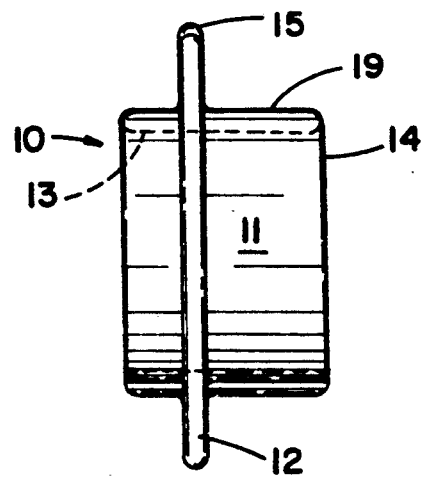
FIG. 4 is a view similar to FIG. 2 rotated 90 degrees.

Referring to the drawings wherein like numerals designate like parts, the preferred embodiment of the invention is a male impotency aid device, generally designated as 10, having a tubular portion 11 and an annular rim 12. In the preferred embodiment, the annular rim 12 and the tubular portion 11 would be made as a single piece formed from a rigid plastic material such as an injection molded styrene plastic. Multiple devices 10 would also be available to a user having varying inside surface 13 diameters in the tubular member 11. Preferrably, these diameters would vary in 0.05 millimeter increments from 27.5 millimeters to 36 millimeter sizes. These varying sizes would allow a physician or the user to select the proper fitting device 10 that would fit snugly but would not strangulate the penis 30.

The tubular portion 11 would have a length between 20 and 40 millimeters, preferably around 27 millimeters, and would have a wall thickness of 4 millimeters. The tubular portion 11 would also have a notch 16 generally located in the bottom portion of the inside surface 13. The notch 16 would have a width of approximately 6 millimeters and a depth of approximately 2 millimeters to correspond and align with the user's penile urinary tract 20. As shown in FIG. 1, when the device is properly applied, the tubular portion 11 would have an end surface 14 that would contact the crus of the penis 18 near pubic bone 17.

In the preferred embodiment, the annular rim 12 would be generally located 15 millimeters from the end surface 14 and would have a thickness of 4 millimeters. The annular rim 12 would also extend between 8 and 10 millimeters beyond the outer surface 19 of the tubular portion 11. This annular rim can be used by the user to slide the device 10 into the proper location. The annular rim 12 also provides another advantage in that it helps to maintain the device 10 in the proper position. Should the device slide forward because of the taper at the base of the penis 30, the thrust from the sex act will force the device 10 back to its proper position.

In the preferred embodiment, the device 10 would also contain a tab 15 located on the top of the annular rim 12 in an axial plane that extends through the notch 16. This tab 15 would be used as a locator when the user applied the device 10 over the penis 30. The user would position the tab 15 such that it was above the upper surface of the penis 30, therefore, insuring that the notch 16 is aligned with the penile urinary tract 20.

When the device 10 is properly positioned on the penis 30, as shown in FIG. 1, the end surface 14 contacts the crus of the penis 18 and stimulates the penis 30. This stimulation causes the main artery in the corpus cavernosum 22 to dilate and increase the bloodflow to the penis 30. As the penis 30 begins to become erect, the rigid shape of the inside surface 13 of the tubular portion 11 helps to partially restrict the return bloodflow through the veins in the corpus cavernosum 22. Therefore, a full erection can be attained and maintained. Unlike many other devices, however, the penile urinary tract 20 in the corpus spongiosum 21 is not constricted because it is located within the notch 16 of the tubular portion 11. Therefore, the user is not prevented or inhibited from ejaculating.

After the sexual act, the pulse rate of the user will lower decreasing the bloodflow to the penis 30. As the bloodflow to the penis 30 decreases, the constriction on the veins will decrease. Because the device 10 has a fixed shape that is not strangulating, the veins are allowed to open and the bloodflow can leave the penis 30. The penis 30 will then reduce in size and the device 10 can be easily removed.

As evidenced by the previous description of the device, the device is small, effective and has thin walls. The device also covers only a small portion of the penis 30. Therefore, the device does not interfere with the enjoyment of either party to the sex act. It is also believed that continued use of the device tends to reactivate the sensory glands in the penis 30 enabling the user to more easily obtain an erection during subsequent uses of the device 10.

Although characteristics and advantages, together with details for structure, materials, function and process steps have been described in reference to a preferred embodiment herein, it is understood that the disclosure is illustrative. To that degree, various changes made, especially to matters of shape, size and arrangement, to the full extent extended by the general meanings of the terms in which the appended claims are expressed, are within the principles of the present invention.

What is claimed is:

1. A male impotency aid device for enabling a man to acquire and maintain an erect penis comprising:

(a) a rigid tubular portion having inner and outer surfaces, wherein the inner surface has a notch extending the length of the tubular member and wherein the diameter of the inner surface is arranged and configured to fit snugly on the penis without strangulation;
   (b) an annular rim extending outward from the outer surface of the tubular portion; and
   (c) an end surface on the tubular portion that comes into contact with the crus of the user's penis, wherein the device further comprises locating means to enable the user to easily position the notch to align with the urinary tract in the bottom of the penis, said locating means is a tab extending outward from the rim that is generally located in an axial plane extending through the notch.

2. A male impotency aid device according to claim 1, wherein the tubular portion and rim are a single piece that is molded from a hard plastic material.

3. A therapeutic method for aiding sexual impotency in men comprising:

(a) providing a male impotency aid device for enabling a man to acquire and maintain an erect penis, said device comprising:
      (i) a rigid tubular portion having inner and outer surfaces, wherein the inner surface has a notch extending the length of the tubular member and wherein the diameter of the inner surface is arranged and configured to fit snugly on the penis without strangulation, and
      (ii) an annular rim extending from the outer surface of the tubular portion;
      (iii) an end surface on the tubular portion that comes into contact with the crus of the user's penis;
      (iv) a locating means to enable the user to easily position the notch to align with the urinary tract in the bottom of the penis, said locating means is a tab extending outward from the rim that is generally located in an axial plane extending through the notch
   (b) placing the apparatus over the penis such that the notch is positioned to be in line with the user's urinary tract; and
   (c) positioning the device on the penis such that the tubular portion is in contact with the crus of the user's penis to stimulate the glans to limit the exit bloodflow from the penis to create an erection.

* * * * *